US005621078A

United States Patent [19]
Riemen et al.

[11] Patent Number: 5,621,078
[45] Date of Patent: Apr. 15, 1997

[54] MODIFIED PSEUDOMONAS EXOTOXIN PE$_{40}$

[75] Inventors: Mark W. Riemen, Carmel, Ind.; Steven M. Stirdivant, Warrington, Pa.

[73] Assignee: Merck & Co., Inc., Rahway, N.J.

[21] Appl. No.: 391,259

[22] Filed: Feb. 21, 1995

Related U.S. Application Data

[63] Continuation of Ser. No. 120,698, Sep. 10, 1993, abandoned, which is a continuation of Ser. No. 879,037, Apr. 30, 1992, abandoned, which is a continuation-in-part of Ser. No. 708,267, Jun. 24, 1991, abandoned, which is a continuation of Ser. No. 327,214, Mar. 22, 1989, abandoned.

[51] Int. Cl.$^6$ ................................................ C07K 14/21
[52] U.S. Cl. ............................................................ 530/350
[58] Field of Search ................................. 530/350, 399, 530/402; 514/2

[56] References Cited

U.S. PATENT DOCUMENTS

| | | | |
|---|---|---|---|
| 4,518,584 | 5/1985 | Mark et al. | 424/85.2 |
| 4,545,985 | 10/1985 | Pastan et al. | 424/180.1 |
| 4,664,911 | 5/1987 | Uhr et al. | |
| 4,675,382 | 6/1987 | Murphy. | |
| 4,742,003 | 5/1988 | Derynck et al. | 435/69.4 |
| 4,892,827 | 1/1990 | Pastan et al. | 435/193 |
| 4,959,314 | 9/1990 | Mark et al. | 435/69.1 |

FOREIGN PATENT DOCUMENTS

| | | |
|---|---|---|
| 0192811 | 9/1986 | European Pat. Off. . |
| 0234599 | 9/1987 | European Pat. Off. . |
| 0261671 | 3/1988 | European Pat. Off. . |
| WO87/02987 | 5/1987 | WIPO . |

OTHER PUBLICATIONS

Proc. Natl. Acad. Sci. USA, vol. 83, pp. 8258–8262 (Nov. 1986) Genetics, by J. R. Murphy, et al., entitled *Genetic construction, expression, and melanoma–selective cytotoxicity of a diphtheria toxin–related α–melanocyte–stiimulating hormone fusion protein.* (Cumulative).

Proc. Natl. Acad. Sci. USA, vol. 85, pp. 3980–3984, (Jun. 1988) Immunology, by V. E. Kelley, entitled *Interleuken 2–kiphtheria toxin fusion protein can abolish cell–mediated immunity in vivo.* (Cumulative).

Proc. Natl. Acad. Sci. USA, vol. 83, pp. 1320–1324, (Mar. 1986), by V. S. Allured, et al., entitled *Structure of exotoxin A of Pseudomonas aeruginosa at 3.0–Ångstrom resolution.* (Cumulative).

Cell, vol. 48, pp. 129–136, (Jan. 16, 1987), J. Hwange, et al., entitled *Functional Domains of Pseudomonas Exotoxin Identified by Deletion Analysis of the Gene Expressed in E. coli.* (Cumulative).

Proc. Natl. Acad. Sci. USA, vol. 84, pp. 4538–4542 (Jul. 1987), by V. K. Chaudhary, et al., entitled *Activity of a recombinant fusion protein between transforming growth factor type α and Pseudomonas toxin.* (Cumulative).

Biotechnology, pp. 1326–1329 (Nov. 1988), by P. Bailon, et al., entitled *Purification and Partial Characterization of an Interleukin 2–Pseudomonas Exotoxin Fusion Protein.* (Cumulative).

Proc. Natl. Acad. Sci. USA, vol. 81, pp. 2645–2649, Biochemistry (May 1984), by G. L. Gray, et al., entitled *Cloning, nucleotide sequence, and expression in Escherichia coli of the exotoxin A structural gene of Pseudomonas aeruginosa.* (Cumulative).

J. of Bio. Chem. vol. 264, No. 24, pp. 14256–14260 (Aug. 25, 1989), by C. B. Siegall, entitled *Functional Analysis of Domains II, Ib, and III of Pseudomonas Exotoxin.* (Cumulative).

Infection & Immunity, vol. 57, No. 7, pp. 1873–1878 (Jul. 1989), by I. H. Madshus, et al., entitled *Effects of Eliminating a Disulfide Bridge within Domain II of Pseudomonas aeruginosa Exotoxin A.* (Cumulative).

Molecular & Cellular Biology, vol. 9, vol. 7, pp. 2860–2867 (Jul. 1989), by G. M. Edwards, entitled *Epidermal Growth Factor Receptor Binding is Affected by Structural Determinants in the Toxin Domain of Transforming Growth Factor–Alpha–Pseudomonas Exotoxin Fusion Proteins.* (Cumulative).

J. of Biol. Chem., vol. 264, No. 26, (Sep. 15, 1989), by I. Pastan, et al., entitled *Pseudomonas Exotoxin: Chimeric Toxins.*

J. of Biol. Chem., vol. 264, No. 27, pp. 15953–15959 (Sep. 25, 1989) by Y. Jinno, et al., entitled *Domain II Mutants of Pseudomonas Exotoxin Deficient in Translocation.*

Proc. Natl. Acad. Sci. USA, vol. 85, pp. 2939–2943, Biochemistry (May 1988), by V. K. Chaudhary, et al., entitled *Role of domain II of Pseudomonas exotoxin in the secretion of proteins into the periplasm and medium by Escherichia coli.*

Schulz et al, *Principles of Protein Structure*, pp. 14–16 (Springer–Verlag, NY 1977).

Rudinger, *Peptide Hormones*, pp. 1–6 (Univ. Park Press, London, 1976).

Hwang et al "Functional Domains of Pseudomonas Exotoxin ... " Cell 48 129–136 Jan. 16, 1987.

Primary Examiner—Marianne P. Allen
Assistant Examiner—Karen E. Brown
Attorney, Agent, or Firm—David A. Muthard; Mark R. Daniel

[57] ABSTRACT

Pseudomonas exotoxin 40 is modified by deleting or substituting one or more cysteine residues. Such a modified protein, when hybridized to TGFα, exhibits altered biological activities from unmodified TGFα PE$_{40}$, including decreased cell killing activity and increased receptor-binding activity.

3 Claims, 1 Drawing Sheet

MODIFIED PSEUDOMONAS EXOTOXIN PE$_{40}$

This application is a continuation, of application Ser. No. 08/120,698, now abandoned, filed Sep. 10, 1993, which is a Continuation Application of 07/879,037 now abandoned, filed Apr. 30, 1992, which was a Continuation-In-Part Application of 07/708,267 filed Jun. 24, 1991, now abandoned, which was a Continuation Application of 07/327,214 filed Mar. 22, 1989, now abandoned.

BACKGROUND OF THE INVENTION

Traditional cancer chemotherapy relies on the ability of drugs to kill tumor cells in cancer patients. Unfortunately, these same drugs frequently kill normal cells as well as the tumor cells. The extent to which a cancer drug kills tumor cells rather than normal cells is an indication of the compound's degree of selectivity for tumor cells. One method of increasing the tumor cell selectivity of cancer drugs is to deliver drugs preferentially to the tumor cells while avoiding normal cell populations. Another term for the selective delivery of chemotherapeutic agents to specific cell populations is "targeting". Drug targeting to tumor cells can be accomplished in several ways. One method relies on the presence of specific receptor molecules found on the surface of tumor cells. Other molecules, referred to as "targeting agents", can recognize and bind to these cell surface receptors. These "targeting agents" include, e.g., antibodies, growth factors, or hormones. "Targeting agents" which recognize and bind to specific cell surface receptors are said to target the cells which possess those receptors. For example, many tumor cells possess a protein on their surfaces called the epidermal growth factor receptor. Several growth factors including epidermal growth factor (EGF) and transforming growth factor-alpha (TGF-alpha) recognize and bind to the EGF receptor on tumor cells. EGF and TGF-alpha are therefore "targeting agents" for these tumor cells.

"Targeting agents" by themselves do not kill tumor cells. Other molecules including cellular poisons or toxins can be linked to "targeting agents" to create hybrid molecules that possess both tumor cell targeting and cellular toxin domains. These hybrid molecules function as tumor cell selective poisons by virtue of their abilities to target tumor cells and then kill those cells via their toxin component. Some of the most potent cellular poisons used in constructing these hybrid molecules are bacterial toxins that inhibit protein synthesis in mammalian cells. Pseudomonas exotoxin A (PE-A) is one of these bacterial toxins, and has been used to construct hybrid "targeting - toxin" molecules (U.S. Pat. No. 4,545,985).

PE-A is a 66 kD bacterial protein which is extremely toxic to mammalian cells. The PE-A molecule contains three functional domains: 1.) The amino-terminal binding domain, responsible for binding to a susceptible cell; 2.) The internally located "translocating" domain, responsible for delivery of the toxin to the cytosol; 3.) The carboxy-terminal enzymatic domain, responsible for cellular intoxication. PE-A has been used in the construction of "targeting-toxin" molecules, anti-cancer agents in which the 66 kD molecule is combined with the tumor-specific "targeting agent" (monoclonal antibody or growth factor). The "targeting-toxin" molecules produced in this manner have enhanced toxicity for cells possessing receptors for the "targeting agent".

A problem with this approach is that the PE-A antibody or growth factor hybrid still has a reasonably high toxicity for normal cells. This toxicity is largely due to the binding of the hybrid protein to cells through the binding domain of the PE-A. In order to overcome this problem, a protein was recombinantly produced which contains only the enzymatic and "translocating" domains of Pseudomonas exotoxin A (Hwang et al., Cell, 48:129–137 1987). This protein was named PE$_{40}$ since it has a molecular weight of 40 kD. PE$_{40}$ lacks the binding domain of PE-A, and is unable to bind to mammalian cells. Thus, PE$_{40}$ is considerably less toxic than the intact 66 kD protein. As a result, hybrid "targeting-toxin" molecules produced with PE$_{40}$ were much more specific in their cellular toxicity (Chaudhary et al., Proc. Nat. Acad. Sci. USA, 84: 4583–4542 1987).

While working with PE$_{40}$, it was found that the cysteine residues at positions 265, 287, 372 and 379 (numbering from the native 66 kD PE-A molecules; Gray et al., Proc. Natl. Acad. Sci., USA, 81, 2645–2649 (1984)) interfered with the construction of "targeting-toxin" molecules using chemical conjugation methods. The reactive nature of the disulfide bonds that these residues form leads to ambiguity with regard to the chemical integrity of the product "targeting toxin".

DISCLOSURE STATEMENT

Figure 1:
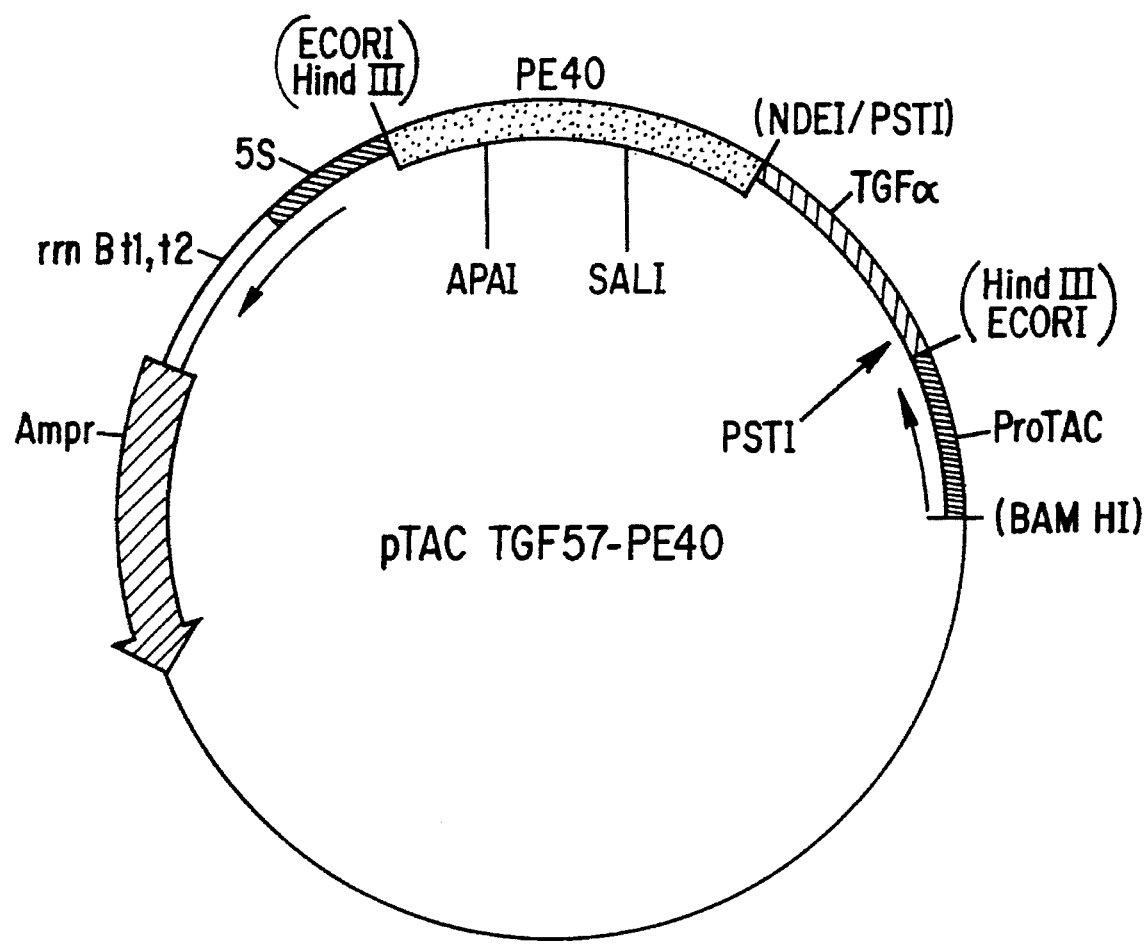
FIG. 1 is a map of plasmid pTACTGF57-PE$_{40}$.

1. U.S. Pat. No. 4,545,985 teaches that pseudomonas exotoxin A can be conjugated to antibodies or to epidermal growth factor. U.S. Pat. No. 4,545,985 further teaches that these conjugates can be used to kill human tumor cells.
2. U.S. Pat. No. 4,664,911 teaches that antibodies can be conjugated to the A chain or the B chain of ricin which is a toxin obtained from plants. U.S. Pat. No. 4,664,911 further teaches, that these conjugates can be used to kill human tumor cells.
3. U.S. Pat. No. 4,675,382 teaches that hormones such as melanocyte stimulating hormone (MSH) can be linked to a portion of the diphtheria toxin protein via peptide bonds. U.S. Pat. No. 4,675,382 further teaches that the genes which encode these proteins can be joined together to direct the synthesis of a hybrid fusion protein using recombinant DNA techniques. This fusion protein has the ability to bind to cells that possess MSH receptors.
4. Murphy et al., PNAS USA 83:8258–8262 1986, Genetic construction, expression, and melanoma-selective cytotoxicity of a diphtheria toxin-related alpha-melanocyte-stimulating hormone fusion protein. This article teaches that a hybrid fusion protein produced in bacteria using recombinant DNA technology and consisting of a portion of the diphtheria toxin protein joined to alpha-melanocyte-stimulating hormone will bind to and kill human melanoma cells.
5. Kelley et al., PNAS USA 85:3980–3984 1988, Interleukin 2-diphtheria toxin fusion protein can abolish cell-mediated immunity in vivo. This article teaches that a hybrid fusion protein produced in bacteria using recombinant DNA technology and consisting of a portion of the diphtheria toxin protein joined to interleukin 2 functions in nude mice to suppress cell mediated immunity.
6. Allured et al., PNAS USA 83:1320–1324 1986, Structure of exotoxin A of Pseudomonas aeruginosa at 3.0 Angstrom. This article teaches the three dimensional structure of the pseudomonas exotoxin A protein.

7. Hwang et al., Cell 48:129–136 1987, Functional Domains of Pseudomonas Exotoxin Identified by Deletion Analysis of the Gene Expressed in *E. Coli*. This article teaches that the pseudomonas exotoxin A protein can be divided into three distinct functional domains responsible for: binding to mammalian cells, translocating the toxin protein across lysosomal membranes, and ADP ribosylating elongation factor 2 inside mammalian cells. This article further teaches that these functional domains correspond to distinct regions of the pseudomonas exotoxin A protein.

8. European patent application 0 261 671 published 30 Mar. 1988 teaches that a portion of the pseudomonas exotoxin A protein can be produced which lacks the cellular binding function of the whole pseudomonas exotoxin A protein but possesses the translocating and ADP ribosylating functions of the whole pseudomonas exotoxin A protein. The portion of the pseudomonas exotoxin A protein that retains the translocating and ADP ribosylating functions of the whole pseudomonas exotoxin A protein is called pseudomonas exotoxin - 40 or PE-40. PE-40 consists of amino acid residues 252–613 of the whole pseudomonas exotoxin A protein as defined in Gray et al., PNAS USA 81:2645–2649 1984. This patent application further teaches that PE-40 can be linked to transforming growth factor-alpha to form a hybrid fusion protein produced in bacteria using recombinant DNA techniques.

9. Chaudhary et al., PNAS USA 84:4538–4542 1987, Activity of a recombinant fusion protein between transforming growth factor type alpha and Pseudomonas exotoxin. This article teaches that hybrid fusion proteins formed between PE-40 and transforming growth factor-alpha and produced in bacteria using recombinant DNA techniques will bind to and kill human tumor cells possessing epidermal growth factor receptors.

10. Bailon et al., Biotechnology, pp. 1326–1329 Nov. 1988. Purification and Partial Characterization of an Interleukin 2-Pseudomonas Exotoxin Fusion Protein. This article teaches that hybrid fusion proteins formed between PE-40 and interleukin 2 and produced in bacteria using recombinant DNA techniques will bind to and kill human cell lines possessing interleukin 2 receptors.

OBJECTS OF THE INVENTION

It is an object of the present invention to provide modifications of $PE_{40}$ which provide improved chemical integrity and defined structure of conjugate molecules formed between "targeting agents" and modified $PE_{40}$. It is another object of this invention to provide a method for preparing and recovering the modified $PE_{40}$ domain from fusion proteins formed between "targeting agents" and modified $PE_{40}$. These and other objects of the present invention will be apparent from the following description.

SUMMARY OF THE INVENTION

The present invention provides modifications of the $PE_{40}$ domain which eliminate the chemical ambiguities caused by the cysteines in $PE_{40}$. Substitution of other amino acids such as, e.g., alanine for the cysteine residues in $PE_{40}$, or deletion of two or more of the cysteine residues improves the biological and chemical properties of the conjugates formed between modified $PE_{40}$ and a targeting agent.

DETAILED DESCRIPTION OF THE INVENTION

Hybrid molecules produced by conjugation of TGFα or EGF and $PE_{40}$ are characterized in three primary assay systems. These assays include: 1—ADP ribosylation of elongation factor 2 which measures the enzymatic activity of EGF-$PE_{40}$ or TGFα-$PE_{40}$ which inhibits mammalian protein synthesis, 2—inhibition of radiolabed EGF binding to the EGF receptor on membrane vesicles from A431 cells which measures the EGF receptor binding activity of EGF-$PE_{40}$, or TGFα $PE_{40}$ and 3—cell viability as assessed by conversion of 3-[4,5-dimethylthiazol-2-yl]-2,5-diphenyltetrazolium bromide (MTT) to formazan which is used to measure the survival of tumor cells following exposure to EGF-$PE_{40}$ or TGFα $PE_{40}$. These assays are performed as previously described (Chung et al., Infection and Immunity, 16:832–841 1977, Cohen et al., J. Biol. Chem., 257:1523–1531 1982, Riemen et al., Peptides 8:877–885 1987, Mossman, J. Immunol. Methods, 65:55–63 1983).

Briefly, to determine peptide binding to the EGF receptor, A431 membrane vesicles were incubated with radio-iodinated peptide; bound and unbound ligand were then separated by rapid filtration which retained the vesicles and associated radioligand. For most assays, the radioligand was $^{125}$I-EGF obtained from New England Nuclear. For some assays, homogeneous (HPLC) EGF was radio-iodinated using Chloramine T.

EGF binding assays were carried out in a total reaction volume of 100 μl in Dulbecco's phosphate-buffered saline (pH 7.4) containing 1% (w/v) Pentax Fraction V Bovine Serum Albumin, 1 nM $^{125}$I-EGF (150 μCi/μg), and shed A431 plasma membrane vesicles (35 μ membrane protein). To assess non-specific binding, 100 nM unlabelled EGF or Peak IV was included in the assay. At time 0, the reaction was initiated by the addition of membrane vesicles. After 30 minutes at 37° C., the vesicles were collected on glass fiber filter mats and washed for 20 seconds with Dulbecco's phosphate-buffered saline, using a Skatron Cell Harvester, Model 7000. $^{125}$I-EGF retained by the filters was then quantitated by gamma spectrometry. Assay points were performed in triplicate.

Specifically, to determine cell killing activity, MTT (3-(4, 5-dimethylthiazol-2-yl)-2,5-diphenyl tetrazolium bromide; Sigma catalog no. M2128) was dissolved in PBS at 5 mg/ml and filtered to sterilize and remove a small amount of insoluble residue present in some batches of MTT. At the times indicated below, stock MTT solution (10 μl per 100 μl medium) was added to all wells of an assay and plates were incubated at 37° C. for 4 h. Acid-isopropanol (100 μl of 0.04N NCl in isopropanol) was added to all wells and mixed thoroughly to dissolve the dark blue crystals. After a few minutes at room temperature to ensure that all crystals were dissolved, the plates were read on a Dynatech MR580 Microelisa reader, using a test wavelength of 570 nm, a reference wavelength of 630 nm, and a calibration setting of 1.99 (or 1.00 if the samples were strongly colored). Plates were normally read within 1 h of adding the isopropanol.

We first produced a series of recombinant DNA molecules that encoded either TGF-alpha - $PE_{40}$ or specifically modified versions of TGF-alpha - $PE_{40}$. The original or parental TGF-alpha - $PE_{40}$ gene was molecularly cloned in a bacterial TAC expression plasmid vector (pTAC TGF57-PE40) using distinct segments of cloned DNA as described in Example 1. The pTAC TGF57-PE40 DNA clone was used as the starting reagent for constructing specifically modified versions of TGF-alpha - $PE_{40}$ DNA. The specific modifications of the pTAC TGF57-$PE_{40}$ DNA involve site specific mutations in the DNA coding sequence required to replace two or four of the cysteine codons within the $PE_{40}$ domain of the pTAC TGF57-PE40 DNA with codons for other amino acids. Alternatively, the site specific mutations can be engineered to delete two or four of the cysteine codons within the PE40 domain of pTAC TGF57-PE40. The site specific mutations in the pTAC TGF57-PE40 DNA were constructed using the methods of Winter et al., Nature 299:756–758 1982. Specific examples of the mutated pTAC TGF57-PE40 DNAs are presented in Example 2.

The amino acid sequence of the parent TGF-alpha - $PE_{40}$ is presented in Sequence ID No. 2. The four cysteine residues in the $PE_{40}$ domain of the parental TGF-alpha - $PE_{40}$ hybrid fusion protein are designated residues $Cys^{265}$, $Cys^{287}$, $Cys^{372}$, and $Cys^{379}$. Amino acid residues are numbered as defined for the native 66 kD PE-A molecule (Gray et al., Proc. Natl. Acad. Sci., USA, 81, 2645–2649 1984). The modified TGF-alpha - $PE_{40}$ fusion proteins used to generate the modified $PE_{40}$ molecules contain substitutions or deletions of residues [$Cys^{265}$ and $Cys^{287}$] or [$Cys^{372}$ and $Cys^{379}$], or [$Cys^{265}$, $Cys^{287}$, $Cys^{372}$, and $Cys^{379}$]. To simplify the nomenclature for the modified $PE_{40}$ molecules generated from the modified fusion proteins, we have designated the amino acid residues at positions 265 and 287 as the "A" locus, and the residues at positions 372 and 379 the "B" locus. When cysteines are present at amino acid residues 265 and 287 as in the parental TGF-alpha - $PE_{40}$ fusion protein, the locus is capitalized (i.e. "A"). When the cysteines are substituted with other amino acids or deleted from residues 265 and 287, the locus is represented by a lower case "a". Similarly, when the amino acid residues at positions 372 and 379 are cysteines, the locus is represented by an upper case "B" while a lower case "b" represents this locus when the amino acid residues at positions 372 or 379 are substituted with other amino acids or deleted. Thus when all four cysteine residues in the $PE_{40}$ domain are substituted with alanines or deleted the modified $PE_{40}$ is designated $PE_{40}$ ab. In a similar fashion the parental $PE_{40}$ derived from the parental TGF-alpha - $PE_{40}$ fusion protein with cysteines at amino acid residue positions 265, 287, 372, and 379 can be designated $PE_{40}$ AB.

The source materials (i.e. the TGF-alpha - $PE_{40}$ AB hybrid protein, and the modified TGF-alpha - $PE_{40}$ Ab, aB and ab hybrid proteins), are produced in *E. coli* using the TAC expression vector system described by Linemeyer et al., Biotechnology 5:960–965 1987. The source proteins produced in these bacteria are harvested and purified by lysing the bacteria in guanidine hydrochloride followed by the addition of sodium sulfite and sodium tetrathionate. This reaction mixture is subsequently dialzyed and urea is added to solubilize proteins which have precipitated from solution. The mixture is centrifuged to remove insoluble material and the recombinant hybrid TGF-alpha - $PE_{40}$ source proteins are separated using ion exchange chromatography, followed by size exclusion chromatography, followed once again by ion exchange chromatography.

Since the single methionine residue in the hybrid source proteins is located between the TGF-alpha and $PE_{40}$ domains, treatment with CNBr would cleave the source proteins, yielding the modified $PE_{40}$ proteins and TGF-alpha. The purified S-sulfonate derivatives of TGF-alpha - $PE_{40}$ are thus subjected to CNBr treatment to remove the TGF portion of the molecule. The desired modified $PE_{40}$ portion is purified by ion-exchange chromatography followed by size exclusion chromatography. The purified modified $PE_{40}$ is then derivatized with a suitable heterobifunctional reagent, e.g. SPDP, to allow conjugation of the desired targeting agent. Following conjugation, size exclusion chromatography is used to isolate the conjugate from non-conjugated materials. Once the purified conjugate is isolated, it is tested for biologic activity using the ADP-ribosylation assay and the relevant receptor binding and cell viability assays.

The following examples illustrate the present invention without, however, limiting the same thereto. All of the enzymatic reactions required for molecular biology manipulations, unless otherwise specified, are carried out as described in Maniatis et al., (1982) In: Molecular Cloning: A Laboratory Manual, Cold Spring Harbor Press.

EXAMPLE 1

Construction of Recombinant DNA Clones Containing TGF-alpha - $PE_{40}$ DNA

The TGF-alpha DNA segment was constructed using three sets of synthetic oligonucleotides as described by Defeo-Jones et al., Molecular and Cellular Biology 8:2999–3007 1988. This synthetic TGF-alpha gene was cloned into pUC-19. DNA from the pUC-19 clone containing recombinant human TGF-alpha was digested with Sph I and Eco RI. The digestion generated a 2.8 kb DNA fragment containing all of pUC-19 and the 5' portion of TGF-alpha. The 2.8 kb fragment was purified and isolated by gel electrophoresis. An Eco RI to Sph I oligonucleotide cassette was synthesized. This synthetic cassette had the sequence indicated in Sequence ID No. 3.

For convenience, this oligonucleotide cassette was named 57. Cassette 57 was annealed and ligated to the TGF-alpha containing 2.8 kb fragment forming a circularized plasmid. Clones which contained the cassette were identified by hybridization to radiolabeled cassette 57 DNA. The presence of human TGF-alpha was confirmed by DNA sequencing. Sequencing also confirmed the presence of a newly introduced Fsp I site at the 3' end of the TGF-alpha sequence. This plasmid, named TGF-alpha-57/pUC-19, was digested with HinD III and Fsp I which generated a 168 bp fragment containing the TGF-alpha gene (TGF-alpha-57). A separate preparation of pUC-19 was digested with HinD III and Eco RI which generated a 2.68 kb pUC-19 vector DNA. The $PE_{40}$ DNA was isolated from plasmid pVC 8 (Chaudhary et al., PNAS USA 84:4538–4542 1987). pVC 8 was digested using Nde I. A flush end was then generated on this DNA by using the standard conditions of the Klenow reaction (Maniatis et al., supra, p.113). The flush-ended DNA was then subjected to a second digestion with Eco RI to generate a 1.3 kb Eco RI to Nde I (flush ended) fragment containing $PE_{40}$. The TGF-alpha-57 HinD III to Fsp I fragment (168 bp) was ligated to the 2.68 kb pUC-19 vector. Following overnight incubation, the 1.3 kb EcoRI to Nde I (flush ended) $PE_{40}$ DNA fragment was added to the ligation mixture. This second ligation was allowed to proceed overnight. The ligation reaction product was then used to transform JM 109 cells. Clones containing TGF-alpha-57 $PE_{40}$ in pUC-19 were identified by hybridization to radiolabeled TGF-alpha-57 $PE_{40}$ DNA and the DNA from this clone was isolated. The TGF-alpha-57 $PE_{40}$ was removed from the pUC-19 vector and transferred to a TAC vector system described by Linemeyer et al., Bio-Technology 5:960–965 1987). The TGF-alpha-57 $PE_{40}$ in pUC-19 was digested with HinD III and Eco RI to generate a 1.5 kb fragment containing TGF-alpha-57 $PE_{40}$. A flush end was generated on this DNA fragment using standard Klenow reaction conditions (Maniatis et al., op. cit.). The TAC vector was digested with HinD III and Eco RI. A flush end was generated on the digested TAC vector DNA using standard Klenow reaction conditions (Maniatis et al., op. cit. The 2.7 kb flush ended vector was isolated using gel electrophoresis.

The flush ended TGF-alpha-57 PE$_{40}$ fragment was then ligated to the flush ended TAC vector. The plasmid generated by this ligation was used to transform JM 109 cells. Candidate clones containing TGF-alpha-57 PE$_{40}$ were identified by hybridization as indicated above and sequenced. The clone containing the desired construction was named pTAC TGF57-PE$_{40}$. The plasmid generated by these manipulations is depicted in FIG. 1. The nucleotide sequence of the amino acid codons of the TGF-alpha - PE$_{40}$ fusion protein encoded in the pTAC TGF-57-PE40 DNA are depicted in Sequence ID No. 1. The amino acid sequence encoded by the TGF-57-PE40 gene is shown in Sequence ID No. 2.

EXAMPLE 2

Construction of Modified Versions of Recombinant TGF-alpha - PE$_{40}$ Containing DNA Clones: Substitution of Alanines for Cysteines.

TGF-alpha - PE$_{40}$ aB:

The clone pTAC TGF57-PE40 was digested with SphI and BamHI and the 750 bp SphI-BamHI fragment (specifying the C-terminal 5 amino acids of TGF-alpha and the N-terminal 243 amino acids of $PE_{40}$) was isolated. M13 mp19 vector DNA was cut with SphI and BamHI and the vector DNA was isolated. The 750 bp SphI-BamHI TGF-alpha - $PE_{40}$ fragment was ligated into the M13 vector DNA overnight at 15° C. Bacterial host cells were transformed with this ligation mixture, candidate clones were isolated and their plasmid DNA was sequenced to insure that these clones contained the proper recombinant DNAs. Single stranded DNA was prepared for mutagenesis.

An oligonucleotide (oligo #132) was synthesized and used in site directed mutagenesis to introduce a HpaI site into the TGF-alpha - $PE_{40}$ DNA at amino acid position 272 of $PE_{40}$:

5' CTGGAGACGTTAACCCGTC 3' (See Sequence ID No. 4)

One consequence of this site directed mutagenesis was the conversion of residue number 272 in $PE_{40}$ from phenylalanine to leucine. The mutagenesis was performed as described by Winter et al., Nature, 299:756–758 1982.

A candidate clone containing the newly created HpaI site was isolated and sequenced to validate the presence of the mutated genetic sequence. This clone was then cut with SphI and SalI. A 210 bp fragment specifying the C-terminal 5 amino acids of TGF-alpha and the N-terminal 70 amino acids of $PE_{40}$ and containing the newly introduced HpaI site was isolated and subcloned back into the parent pTAC TGF57-PE40 plasmid at the SphI-SalI sites. Bacterial host cells were transformed, a candidate clone was isolated and its plasmid DNA was sequenced to insure that this clone contained the proper recombinant DNA. For convenience this clone was named pTAC TGF57-PE40-132. pTAC TGF57-PE40-132 was digested with SphI and HpaI and a 3.96 Kb DNA fragment was isolated. A synthetic oligonucleotide cassette (oligo #153 See Sequence ID No. 5) spanning the C-terminal 5 amino acids of TGF-alpha and the N-terminal 32 amino acids of $PE_{40}$ and containing SphI and HpaI compatible ends was synthesized and ligated to the digested pTAC TGF57-PE40-132.

This oligonucleotide cassette incorporated a change in the TGF-alpha - $PE_{40}$ DNA so that the codon specifying cysteine at residue 265 now specified alanine. For convenience this plasmid DNA was called pTAC TGF57-PE40-132,153. Bacterial host cells were transformed with pTAC TGF57-PE40-132,153 DNA. Candidate clones were identified by hybridization, isolated and their plasmid DNA was sequenced to insure that it contained the proper recombinant DNA.

pTAC TGF57-PE40-132,153 DNA was digested with HpaI and SalI and a 3.95 Kb vector DNA was isolated. A synthetic oligonucleotide cassette (oligo #142 see Sequence ID No. 6) spanning amino acid residues 272 to 309 of $PE_{40}$ and containing HpaI and SalI compatible ends was synthesized and ligated to the 3.95 Kb pTAC TGF/PE40 132,153 DNA.

This oligonucleotide cassette changes the codon specifying cysteine at residue 287 so that this codon now specifies alanine. For convenience this mutated plasmid DNA was called pTAC TGF57-PE40-132,153,142. Bacterial host cells were transformed with this plasmid and candidate clones were identified by hybridization. These clones were isolated and their plasmid DNA was sequenced to insure that it contained the proper recombinant DNA. The pTAC TGF57-PE40-132,153,142 plasmid encodes the TGF-alpha - $PE_{40}$ variant with both cysteines at locus "A" replaced by alanines. Therefore, following the nomenclature described previously this modified version of TGF-alpha - $PE_{40}$ is called TGF-alpha - $PE_{40}$ aB. The amino acid sequence encoded by the TGF-alpha-$PE_{40}$ aB gene is shown in Sequence ID No. 7.

TGF-alpha - $PE_{40}$ Ab:

The clone pTAC TGF57-$PE_{40}$ was digested with SphI and BamHI and the 750 bp SphI-BamHI fragment (specifying the C-terminal 5 amino acids of TGF-alpha and the N-terminal 252 amino acids of PE40) was isolated. M13 mp19 vector DNA was cut with SphI and BamHI and the vector DNA was isolated. The 750 bp SphI-BamHI TGF-alpha - $PE_{40}$ fragment was ligated into the M13 vector DNA overnight at 15° C. Bacterial host cells were transformed with this ligation mixture, candidate clones were isolated and their plasmid DNA was sequenced to insure that these clones contained the proper recombinant DNAs. Single stranded DNA was prepared for mutagenesis.

An oligonucleotide (oligo #133 Sequence ID No. 8) was synthesized and used in site directed mutagenesis to introduce a BsteII site into the TGF-alpha - $PE_{40}$ DNA at amino acid position 369 of $PE_{40}$.

One consequence of this mutagenesis was the conversion of the serine residue at position 369 of $PE_{40}$ to a threonine.

A DNA clone containing the newly created BsteII site was identified, isolated and sequenced to ensure the presence of the proper recombinant DNA. This clone was next digested with ApaI and SalI restriction enzymes. A 120 bp insert DNA fragment containing the newly created BsteII site was isolated and ligated into pTAC TGF57-PE40 that had also been digested with ApaI and SalI. Bacterial host cells were transformed, and a candidate clone was isolated and sequenced to insure that the proper recombinant DNA was present. This newly created plasmid DNA was called pTAC TGF57-PE40-133. It was digested with BsteII and ApaI and 2.65 Kb vector DNA fragment was isolated.

A BsteII to ApaI oligonucleotide cassette (oligo #155 Sequence ID No. 9) was synthesized which spanned the region of TGF-alpha - $PE_{40}$ deleted from the pTAC TGF57-PE40-133 clone digested with BsteII and ApaI restriction enzymes. This cassette also specified the nucleotide sequence for BsteII and ApaI compatible ends.

This oligonucleotide cassette changed the codons for cysteines at residues 372 and 379 of $PE_{40}$ to codons specifying alanines. Oligonucleotide cassette #155 was ligated to the 2.65 Kb vector DNA fragment. Bacterial host cells were transformed and candidate clones were isolated and sequenced to insure that the proper recombinant DNA was present. This newly created DNA clone was called pTAC TGF57-PE40-133,155. It encodes the TGF-alpha - $PE_{40}$ variant with both cysteines at locus "B" replaced by alanines. Therefore, following the nomenclature described previously this modified version of TGF-alpha - $PE_{40}$ is called TGF-alpha - $PE_{40}$ Ab. The amino acid sequence encoded by the TGF-alpha-$PE_{40}$ Ab gene is shown in Sequence ID No. 10.

TGF-alpha - $PE_{40}$ ab:

The pTAC-TGF57-PE40-132,153,142 plasmid encoding TGF-alpha - $PE_{40}$ aB was digested with SalI and ApaI and the resultant 3.8 Kb vector DNA fragment was isolated. The pTAC TGF57-PE40-133,155 plasmid encoding TGF-alpha - $PE_{40}$ Ab was also digested with SalI and ApaI and the resultant 140 bp DNA fragment containing the cysteine to alanine changes at amino acid residues 372 and 379 of $PE_{40}$ was isolated. These two DNAs were ligated together and used to transform bacterial host cells. Candidate clones were identified by hybridization with a radiolabeled 140 bp DNA from pTAC TGF57-PE40-133,155. Plasmid DNA from the candidate clones was isolated and sequenced to insure the presence of the proper recombinant DNA. This newly created DNA clone was called pTAC TGF57-PE40-132,153, 142,133,155. This plasmid encodes the TGF-alpha - $PE_{40}$ variant with all four cysteines at loci "A" and "B" replaced by alanines. Therefore, following the nomenclature described previously this modified version of TGF-alpha - $PE_{40}$ is called TGF-alpha - $PE_{40}$ ab. The amino acid sequence encoded by the TGF-alpha-$PE_{40}$ ab gene is shown in Sequence ID No. 11.

EXAMPLE 3

Production and Isolation of Recombinant
TGF-alpha - $PE_{40}$ Source Proteins

Transformed *E. coli* JM-109 cells were cultured in 1 L shake flasks in 500 mL LB-Broth in the presence of 100 ug/mL ampicillin at 37° C. After the $A_{600}$ spectrophotometric absorbance value reached 0.6, isopropyl B-D-thiogalactopyranoside was added to a final concentration of 1 mM. After 2 hours the cells were harvested by centrifugation.

The cells were lysed in 8M guanidine hydrochloride, 50 mM Tris, 1 mM EDTA, pH 8.0 by stirring at room temperature for 2 hours. The lysis mixture was brought to 0.4M sodium sulfite and 0.1M sodium tetrathionate by adding solid reagents and the pH was adjusted to 9.0 with 1M NaOH. The reaction was allowed to proceed at room temperature for 16 hours.

The protein solution was dialysed against a 10,000 fold excess volume of 1 mM EDTA at 4° C. The mixture was then brought to 6M urea, 50 mM NaCl, 50 mM Tris, pH 8.0, at room temperature and stirred for 2 hours. Any undissolved material was removed by centrifugation at 32,000×g for 30 minutes.

The cleared supernatant from the previous step was applied to a 26×40 cm DEAE Sepharose Fast-Flow column (Pharmacia LKB Biotechnology, Inc.) equilibrated with 6M urea, 50 mM Tris, 50 mM NaCl, pH 8.0, at a flow rate of 1 mL/minute. The column was washed with the equilibration buffer until all unadsorbed materials were removed as evidenced by a UV $A_{280}$ spectrophotometric absorbance below 0.1 in the equilibration buffer as it exits the column. The adsorbed fusion protein was eluted from the column with a 1000 mL 50–350 mM NaCl gradient and then concentrated in a stirred cell Amicon concentrator fitted with a YM-30 membrane.

The concentrated fusion protein (8 mL) was applied to 2.6×100 cm Sephacryl S-300 column (Pharmacia LKB Biotechnology, Inc.) equilibrated with 6M urea, 50 mM Tris, 50 mM NaCl, pH 8.0, at a flow rate of 0.25 mL/minute. The column was eluted with additional equilibration buffer and 3 mL fractions collected. Fractions containing TGF-alpha - $PE_{40}$ activity were pooled.

The pooled fractions from the S-300 column were applied to a 1.6×40 cm Q Sepharose Fast-Flow column (Pharmacia LKB Biotechnology, Inc.) equilibrated with 6M urea, 50 mM Tris, 50 mM NaCl, pH 8.0 at a flow rate of 0.7 mL/minute. The column was washed with the equilibration buffer and then eluted with a 600 mL 50–450 mM NaCl gradient. The fractions containing the TGF-alpha - $PE_{40}$ activity were pooled and then dialyzed against 50 mM glycine pH 9.0 and stored at −20° C.

EXAMPLE 4

CNBR Cleavage of TGF-alpha - $PE_{40}$ Source
Proteins and Isolation of Modified $PE_{40}$s ($PE_{40}$ AB,
$PE_{40}$ Ab, $PE_{40}$ aB, $PE_{40}$ab).

The desired fusion protein, still in the S-sulfonated form, is dialysed versus 10% (v/v) acetic acid in water, then lyophilized. The lyophilized protein is dissolved in a sufficient amount of deaerated 0.1M HCl to give a protein concentration of 1 mg/mL. The protein/HCl solution contains 5 moles tryptophan/mole fusion protein. CNBr (500 equivalents per equivalent of methionine) is added, and the reaction allowed to proceed for 18 hours, at room temperature in the dark. Large digestion fragments, including the desired modified $PE_{40}$, are then separated from the reaction mixture by gel filtration (e.g., Sephadex G-25) in 25% acetic acid (v/v). Fractions containing the modified $PE_{40}$ are pooled and lyophilized.

In the case of the modified proteins containing cysteine (i.e $PE_{40}$ AB, $PE_{40}$ aB, and $PE_{40}$ Ab) it is necessary to form the requisite disulfide bonds before proceeding with purification. The lyophilized protein is therefore dissolved in a sufficient amount of 50 mM glycine, pH 10.5 to give a UV $A_{280}$=0.1. Beta-mercaptoethanol is added to give a 4:1 molar ratio over the theoretical number of S-sulfonate groups present in the protein sample. The reaction is allowed to proceed for 16 hours at 4° C., after which time the solution is dialysed against a 10,000 fold excess of a buffer containing 20 mM Tris, i mM EDTA, 100 mM NaCl, pH 8.0.

Fractions from the anion exchange column containing the desired $PE_{40}$ are pooled based on ADP-ribosylation activity and protein content as determined by SDS-PAGE. The pooled fractions are concentrated using a 30,000 molecular weight cutoff membrane (YM-30, Amicon).

The pooled fractions are applied to a 2.6×100 cm Sephacryl S-200 gel filtration column (Pharmacia LKB Biotechnology, Inc.), equilibrated in, and eluted with 20 mM Tris, 50 mM NaCl, 1 mM EDTA, pH 8.0 at a flow rate of 0.75 mL/minute. Fractions from the gel filtration chromatography are pooled based on ADP-ribosylation and SDS-PAGE.

Though this procedure yields material sufficiently pure for most purposes, another chromatographic step is included in order to produce highly homogeneous material. This final chromatographic step is high resolution gel filtration, using a 0.75×60 cm Bio-Sil TSK-250 column (Bio-Rad). In preparation for chromatography on the TSK-250 column, samples are concentrated on Centriprep-30 devices (Amicon) and protein concentration adjusted to 5 mg/mL. The sample is dissolved in 6M urea, 100 mM sodium phosphate, 100 mM NaCl, pH 7.1. The column is eluted with 6M urea, 100 mM sodium phosphate, 100 mM NaCl, pH 7.1, at a flow rate of 0.5 mL/minute. Fractions from the high resolution gel filtration step are pooled based on ADP-ribosylation and SDS-PAGE.

EXAMPLE 5

Conjugation of EGF to Modified $PE_{40}s$ and Isolation of Conjugates

In order to conjugate EGF to modified $PE_{40}$, it is necessary to derivatize both the EGF and PE40 with heterobifunctional agents, so that a covalent connection between the two molecules can be achieved. In preparation for the derivatization, samples of modified $PE_{40}$ are dialyzed against 0.1M NaCl, 0.1M sodium phosphate, pH 7.0. Following dialysis, the solution of modified $PE_{40}$ is adjusted to 4 mg/mL $PE_{40}$ using the dialysis buffer, giving a concentration of 100 uM. A sufficient amount of a 20 mM solution of N-succinimidyl 3-(3-pyridyldithio)propionate (SPDP, Pierce) in ethanol is added to the protein solution to give a final concentration of 300 uM SPDP. This concentration represents a 3:1 ratio of SPDP to $PE_{40}$. The derivatization reaction is allowed to proceed at room temperature for 30 minutes, with occasional agitation of the mixture. The reaction is terminated by adding a large excess of glycine (approximately a 50-fold molar excess over the initial amount of SPDP). The resulting 3-(2-pyridyldithio)propionyl-derivative is called PDP-$PE_{40}$. The non-protein reagents are removed from the product by extensive dialysis versus 6M urea, 0.1M NaCl, 0.1M sodium phosphate, pH 7.5. The number of PDP-groups introduced into the modified $PE_{40}$ is determined as described by Carlsson et al., Biochem. J., 173:723–737 1978.

The PDP-EGF derivative is prepared by dissolving lyophilized EGF (Receptor grade, Collaborative Research) in a sufficient amount of 0.1M NaCl, 0.1M sodium phosphate, pH 7.0 to give a final concentration of 150 uM EGF. A sufficient amount of a 20 mM solution of SPDP in ethanol is added to the EGF solution to give a final concentration of 450 uM SPDP, representing a 3:1 ratio of SPDP to EGF. The derivatization reaction is allowed to proceed at room temperature for 30 minutes, with occasional agitation of the mixture. The reaction is terminated by adding a large excess of glycine (approximately a 50-fold molar excess over the initial amount of SPDP). The non-protein reagents are removed from the product by extensive dialysis versus 6M urea, 0.1M NaCl, 0.1M sodium phosphate, pH 7.5. The number of PDP-groups introduced into EGF is determined as described by Carlsson et al., Biochem. J., 173:723–737 1978.

Using the derivatives described above, either PDP-$PE_{40}$ or PDP-EGF can be reduced at acidic pH, in order to generate the 3-thiopropionyl derivative, in the presence of the intact, native disulfides (Carlsson et al., supra). However, the preferred strategy is the generation of a free thiol on the modified $PE_{40}$.

PDP-$PE_{40}$ (0.4 ml of a 100 uM solution of PDP-$PE_{40}$ in 6M urea, 0.1M NaCl, 0.1M sodium phosphate, pH 7.5) is dialyzed against several 500 mL changes of a buffer containing 6M urea, 25 mM sodium acetate, pH 5.5, at 4° C. Following the dialysis, 20 uL of 100 mM dithiothreitol (final concentration 5 mM) is added to the PDP-$PE_{40}$. The reduction is allowed to proceed for 10 minutes at room temperature, and is then terminated by dialysis of the reaction mixture against 6M urea, 25 mM sodium acetate, 1 mM EDTA, pH 5.5, at 4° C. Dialysis against this buffer is repeated, and then the sample is dialyzed against 0.1M NaCl, 0.1M sodium phosphate, pH 7.5. The material generated by these manipulations is called thiopropionyl-$PE_{40}$.

In preparation for conjugation, PDP-EGF (0.8 mL of a 150 uM solution in 6M urea, 0.1M NaCl, 0.1M sodium phosphate, pH 7.5) is dialyzed against several changes of 0.1M NaCl, 0.1M sodium phosphate, pH 7.5, at 4° C., to free the sample of urea. Following this dialysis, the PDP-EGF solution and the thiopropionyl-$PE_{40}$ solution are combined and the reaction mixture is incubated at room temperature for 1 hour. The progress of the reaction can be monitored by measuring the release of pyridine-2-thione as described (Carlsson et al., supra). The reaction is terminated by dialysis against several changes of 6M urea, 0.1M NaCl, 0.1M sodium phosphate, pH 7.5, at 4° C.

The conjugates are purified by size exclusion chromatography, using a high resolution 0.75×60 cm Bio-Sil TSK-250 column (Bio-Rad). The column is eluted with 6M urea, 0.1M sodium phosphate, 0.1M NaCl, pH 7.1, at a flow rate of 0.5 mL/minute. Fractions from the high resolution gel filtration step are pooled based on ADP-ribosylation and SDS-PAGE.

Biological Activities of TGF-alpha - $PE_{40}$ AB, TGF-alpha - $PE_{40}$ Ab, TGF-alpha - $PE_{40}$ aB, and TGF-alpha - $PE_{40}$ ab Proteins The hybrid fusion proteins TGF-alpha-$PE_{40}$ AB, TGF-alpha - $PE_{40}$ Ab, TGF-alpha - $PE_{40}$ aB, TGF-alpha - $PE_{40}$ ab were expressed in bacterial hosts and isolated as described above. Each protein was then characterized for its ability to inhibit the binding of radiolabeled epidermal growth factor to the epidermal growth factor receptor on A431 cell membrane vesicles and for its ability to kill A431 cells as measured in MTT cell proliferation assays. The following table summarizes the biological activities of these proteins:

| | EPIDERMAL GROWTH FACTOR RECEPTOR BINDING $IC_{50}$ nM | A431 CELL KILLING $EC_{50}$ pM |
|---|---|---|
| TGF-alpha - $PE_{40}$ AB | 346 | 47 |
| TGF-alpha - $PE_{40}$-AB | 588 | 25 |
| TGF-alpha - PE40 aB | 27 | 151 |
| TGF-alpha - PE40 ab | 60 | 392 |

What is claimed is:

1. A modified $PE_{40}$ polypeptide selected from the group consisting of $PE_{40}$aB and $PE_{40}$ab, wherein the $PE_{40}$aB is a $PE_{40}$ polypeptide that comprises an alanine at residues 265 and 287 and wherein the PE40ab is a $PE_{40}$ polypeptide that comprises an alanine at residues 265, 287, 372 and 379.

2. The modified $PE_{40}$ polypeptide according to claim 1 which is $PE_{40}$aB.

3. The modified $PE_{40}$ polypeptide according to claim 1 which is $PE_{40}$ab.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
   ( A ) LENGTH: 1260 base pairs
   ( B ) TYPE: nucleic acid
   ( C ) STRANDEDNESS: single
   ( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

| | | | | | | |
|---|---|---|---|---|---|---|
| ATGGCTGCAG | CAGTGGTGTC | CCATTTTAAT | GACTGCCCAG | ATTCCCACAC | TCAGTTCTGC | 60 |
| TTCCATGGAA | CATGCAGGTT | TTTGGTGCAG | GAGGACAAGC | CGGCATGTGT | CTGCCATTCT | 120 |
| GGGTACGTTG | GTGCGCGCTG | TGAGCATGCG | GACCTCCTGG | CTGCTATGGC | CGAAGAGGGC | 180 |
| GGCAGCCTGG | CCGCGCTGAC | CGCGCACCAG | GCTTGCCACC | TGCCGCTGGA | GACTTTCACC | 240 |
| CGTCATCGCC | AGCCGCGCGG | CTGGGAACAA | CTGGAGCAGT | GCGGCTATCC | GGTGCAGCGG | 300 |
| CTGGTCGCCC | TCTACCTGGC | GGCGCGGCTG | TCGTGGAACC | AGGTCGACCA | GGTGATCCGC | 360 |
| AACGCCCTGG | CCAGCCCCGG | CAGCGGCGGC | GACCTGGGCG | AAGCGATCCG | CGAGCAGCCG | 420 |
| GAGCAGGCCC | TGGCCCTGAC | CCTGGCCGCC | GCCGAGAGCG | AGCGCTTCGT | CCGGCAGGGC | 480 |
| ACCGGCAACG | ACGAGGCCGG | CGCGGCCAAC | GCCGACGTGG | TGAGCCTGAC | CTGCCCGGTC | 540 |
| GCCGCCGGTG | AATGCGCGGG | CCCGGCGGAC | AGCGGCGACG | CCCTGCTGGA | GCGCAACTAT | 600 |
| CCCACTGGCG | CGGAGTTCCT | CGGCGACGGC | GGCGACGTCA | GCTTCAGCAC | CCGCGGCACG | 660 |
| CAGAACTGGA | CGGTGGAGCG | GCTGCTCCAG | GCGCACCGCC | AACTGGAGGA | GCGCGGCTAT | 720 |
| GTGTTCGTCG | GCTACCACGG | CACCTTCCTC | GAAGCGGCGC | AAAGCATCGT | CTTCGGCGGG | 780 |
| GTGCGCGCGC | GCAGCCAGGA | CCTCGACGCG | ATCTGGCGCG | GTTTCTATAT | CGCCGGCGAT | 840 |
| CCGGCGCTGG | CCTACGGCTA | CGCCCAGGAC | CAGGAACCCG | ACGCACGCGG | CCGGATCCGC | 900 |
| AACGGTGCCC | TGCTGCGGGT | CTATGTGCCG | CGCTCGAGCC | TGCCGGGCTT | CTACCGCACC | 960 |
| AGCCTGACCC | TGGCCGCGCC | GGAGGCGGCG | GGCGAGGTCG | AACGGCTGAT | CGGCCATCCG | 1020 |
| CTGCCGCTGC | GCCTGGACGC | CATCACCGGC | CCCGAGGAGG | AAGGCGGGCG | CCTGGAGACC | 1080 |
| ATTCTCGGCT | GGCCGCTGGC | CGAGCGCACC | GTGGTGATTC | CCTCGGCGAT | CCCCACCGAC | 1140 |
| CCGCGCAACG | TCGGCGGCGA | CCTCGACCCG | TCCAGCATCC | CGACAAGGA | ACAGGCGATC | 1200 |
| AGCGCCCTGC | CGGACTACGC | CAGCCAGCCC | GGCAAACCGC | CGCGCGAGGA | CCTGAAGTAA | 1260 |

( 2 ) INFORMATION FOR SEQ ID NO:2:

( i ) SEQUENCE CHARACTERISTICS:
   ( A ) LENGTH: 420 amino acids
   ( B ) TYPE: amino acid
   ( C ) STRANDEDNESS: single
   ( D ) TOPOLOGY: linear ( i i ) MOLECULE TYPE: protein ( x i ) SEQUENCE DESCRIPTION: SEQ ID NO:2:

Met Ala Ala Ala Val Val Ser His Phe Asn Asp Cys Pro Asp Ser His

```
  1                     5                          10                         15

Thr  Gln  Phe  Cys  Phe  His  Gly  Thr  Cys  Arg  Phe  Leu  Val  Gln  Glu  Asp
               20                       25                       30

Lys  Pro  Ala  Cys  Val  Cys  His  Ser  Gly  Tyr  Val  Gly  Ala  Arg  Cys  Glu
               35                       40                       45

His  Ala  Asp  Leu  Leu  Ala  Ala  Met  Ala  Glu  Glu  Gly  Gly  Ser  Leu  Ala
          50                       55                       60

Ala  Leu  Thr  Ala  His  Gln  Ala  Cys  His  Leu  Pro  Leu  Glu  Thr  Phe  Thr
65                       70                       75                       80

Arg  His  Arg  Gln  Pro  Arg  Gly  Trp  Glu  Gln  Leu  Glu  Gln  Cys  Gly  Tyr
                    85                       90                       95

Pro  Val  Gln  Arg  Leu  Val  Ala  Leu  Tyr  Leu  Ala  Ala  Arg  Leu  Ser  Trp
               100                      105                      110

Asn  Gln  Val  Asp  Gln  Val  Ile  Arg  Asn  Ala  Leu  Ala  Ser  Pro  Gly  Ser
               115                      120                      125

Gly  Gly  Asp  Leu  Gly  Glu  Ala  Ile  Arg  Glu  Gln  Pro  Glu  Gln  Ala  Arg
     130                      135                      140

Leu  Ala  Leu  Thr  Leu  Ala  Ala  Ala  Glu  Ser  Glu  Arg  Phe  Val  Arg  Gln
145                      150                      155                      160

Gly  Thr  Gly  Asn  Asp  Glu  Ala  Gly  Ala  Ala  Asn  Ala  Asp  Val  Val  Ser
               165                      170                      175

Leu  Thr  Cys  Pro  Val  Ala  Ala  Gly  Glu  Cys  Ala  Gly  Pro  Ala  Asp  Ser
               180                      185                      190

Gly  Asp  Ala  Leu  Leu  Glu  Arg  Asn  Tyr  Pro  Thr  Gly  Ala  Glu  Phe  Leu
          195                      200                      205

Gly  Asp  Gly  Gly  Asp  Val  Ser  Phe  Ser  Thr  Arg  Gly  Thr  Gln  Asn  Trp
     210                      215                      220

Thr  Val  Glu  Arg  Leu  Leu  Gln  Ala  His  Arg  Gln  Leu  Glu  Glu  Arg  Gly
225                      230                      235                      240

Tyr  Val  Phe  Val  Gly  Tyr  His  Gly  Thr  Phe  Leu  Glu  Ala  Ala  Gln  Ser
               245                      250                      255

Ile  Val  Phe  Gly  Gly  Val  Arg  Ala  Arg  Ser  Gln  Asp  Leu  Asp  Ala  Ile
               260                      265                      270

Trp  Arg  Gly  Phe  Tyr  Ile  Ala  Gly  Asp  Pro  Ala  Leu  Ala  Tyr  Gly  Tyr
          275                      280                      285

Ala  Gln  Asp  Gln  Glu  Pro  Asp  Ala  Arg  Gly  Arg  Ile  Arg  Asn  Gly  Ala
     290                      295                      300

Leu  Leu  Arg  Val  Tyr  Val  Pro  Arg  Ser  Ser  Leu  Pro  Gly  Phe  Tyr  Arg
305                      310                      315                      320

Thr  Ser  Leu  Thr  Leu  Ala  Ala  Pro  Glu  Ala  Ala  Gly  Glu  Val  Glu  Arg
               325                      330                      335

Leu  Ile  Gly  His  Pro  Leu  Pro  Leu  Arg  Leu  Asp  Ala  Ile  Thr  Gly  Pro
               340                      345                      350

Glu  Glu  Glu  Gly  Gly  Arg  Leu  Glu  Thr  Ile  Leu  Gly  Trp  Pro  Leu  Ala
          355                      360                      365

Glu  Arg  Thr  Val  Val  Ile  Pro  Ser  Ala  Ile  Pro  Thr  Asp  Pro  Arg  Asn
     370                      375                      380

Val  Gly  Gly  Asp  Leu  Asp  Pro  Ser  Ser  Ile  Pro  Asp  Lys  Glu  Gln  Ala
385                      390                      395                      400

Ile  Ser  Ala  Leu  Pro  Asp  Tyr  Ala  Ser  Gln  Pro  Gly  Lys  Pro  Pro  Arg
               405                      410                      415

Glu  Asp  Leu  Lys
          420
```

( 2 ) INFORMATION FOR SEQ ID NO:3:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

```
CGGACCTCCT GGCTGCGCAT CTAGG                                           25
```

( 2 ) INFORMATION FOR SEQ ID NO:4:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

```
CTGGAGACGT TAACCCGTC                                                  19
```

( 2 ) INFORMATION FOR SEQ ID NO:5:

( i ) SEQUENCE CHARACTERISTICS:
        ( A ) LENGTH: 84 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

```
CGGACCTCCT GGCCATGGCC GAAGAGGGCG GCAGCCTGGC CGCGCTGACC GCGCACCAGC     60

TGCACACCTG CCGCTGGAGA CGTT                                            84
```

( 2 ) INFORMATION FOR SEQ ID NO:6:

( i ) SEQUENCE CHARACTERISTICS:
        ( A ) LENGTH: 107 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

```
AACCCGTCAT CGCCAGCCGC GCGGCTGGGA ACAACTGGAG CAGGCTGGCT ATCCGGTGCA     60

GCGGCTGGTC GCCCTCTACC TGGCGGCGCG GCTGTCGTGG AACCAGG                  107
```

( 2 ) INFORMATION FOR SEQ ID NO:7:

( i ) SEQUENCE CHARACTERISTICS:
        ( A ) LENGTH: 420 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:7:

```
Met Ala Ala Ala Val Val Ser His Phe Asn Asp Cys Pro Asp Ser His
 1               5                  10                  15
```

```
Thr Gln Phe Cys Phe His Gly Thr Cys Arg Phe Leu Val Gln Glu Asp
         20                  25                  30

Lys Pro Ala Cys Val Cys His Ser Gly Tyr Val Gly Ala Arg Cys Glu
         35                  40                  45

His Ala Asp Leu Leu Ala Ala Met Ala Glu Glu Gly Gly Ser Leu Ala
50                       55                  60

Ala Leu Thr Ala His Gln Ala Ala His Leu Pro Leu Glu Thr Leu Thr
65                  70                  75                  80

Arg His Arg Gln Pro Arg Gly Trp Glu Gln Leu Glu Gln Ala Gly Tyr
                 85                  90                  95

Pro Val Gln Arg Leu Val Ala Leu Tyr Leu Ala Ala Arg Leu Ser Trp
             100                 105                 110

Asn Gln Val Asp Gln Val Ile Arg Asn Ala Leu Ala Ser Pro Gly Ser
             115                 120                 125

Gly Gly Asp Leu Gly Glu Ala Ile Arg Glu Gln Pro Glu Gln Ala Arg
130                 135                 140

Leu Ala Leu Thr Leu Ala Ala Ala Glu Ser Glu Arg Phe Val Arg Gln
145                 150                 155                 160

Gly Thr Gly Asn Asp Glu Ala Gly Ala Ala Asn Ala Asp Val Val Ser
                 165                 170                 175

Leu Thr Cys Pro Val Ala Ala Gly Glu Cys Ala Gly Pro Ala Asp Ser
             180                 185                 190

Gly Asp Ala Leu Leu Glu Arg Asn Tyr Pro Thr Glu Ala Glu Phe Leu
         195                 200                 205

Gly Asp Gly Gly Asp Val Ser Phe Ser Thr Arg Gly Thr Gln Asn Trp
         210                 215                 220

Thr Val Glu Arg Leu Leu Gln Ala His Arg Gln Leu Glu Glu Arg Gly
225                 230                 235                 240

Tyr Val Phe Val Gly Tyr His Gly Thr Phe Leu Glu Ala Ala Gln Ser
                 245                 250                 255

Ile Val Phe Gly Gly Val Arg Ala Arg Ser Gln Asp Leu Asp Ala Ile
             260                 265                 270

Trp Arg Gly Phe Tyr Ile Ala Gly Asp Pro Ala Leu Ala Tyr Gly Tyr
         275                 280                 285

Ala Gln Asp Gln Glu Pro Asp Ala Arg Gly Arg Ile Arg Asn Gly Ala
290                 295                 300

Leu Leu Arg Val Tyr Val Pro Arg Ser Ser Leu Pro Gly Phe Tyr Arg
305                 310                 315                 320

Thr Ser Leu Thr Leu Ala Ala Pro Glu Ala Ala Gly Glu Val Glu Arg
             325                 330                 335

Leu Ile Gly His Pro Leu Pro Leu Arg Leu Asp Ala Ile Thr Gly Pro
             340                 345                 350

Glu Glu Glu Gly Gly Arg Leu Glu Thr Ile Leu Gly Trp Pro Leu Ala
         355                 360                 365

Glu Arg Thr Val Val Ile Pro Ser Ala Ile Pro Thr Asp Pro Arg Asn
370                 375                 380

Val Gly Gly Asp Leu Asp Pro Ser Ser Ile Pro Asp Lys Glu Gln Ala
385                 390                 395                 400

Ile Ser Ala Leu Pro Asp Tyr Ala Ser Gln Pro Gly Lys Pro Pro Arg
                 405                 410                 415

Glu Asp Leu Lys
         420
```

( 2 ) INFORMATION FOR SEQ ID NO:8:

( i ) SEQUENCE CHARACTERISTICS:
    ( A ) LENGTH: 17 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:8:

GACGTGGTGA CCCTGAC  17

( 2 ) INFORMATION FOR SEQ ID NO:9:

( i ) SEQUENCE CHARACTERISTICS:
        ( A ) LENGTH: 43 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

GTGACCCTGA CCGCGCCGGT CGCCGCCGGT GAAGCTGCGG GCC  43

( 2 ) INFORMATION FOR SEQ ID NO:10:

( i ) SEQUENCE CHARACTERISTICS:
        ( A ) LENGTH: 420 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:10:

```
Met Ala Ala Ala Val Val Ser His Phe Asn Asp Cys Pro Asp Ser His
 1               5                  10                  15

Thr Gln Phe Cys Phe His Gly Thr Cys Arg Phe Leu Val Gln Glu Asp
            20                  25                  30

Lys Pro Ala Cys Val Cys His Ser Gly Tyr Val Gly Ala Arg Cys Glu
        35                  40                  45

His Ala Asp Leu Leu Ala Ala Met Ala Glu Glu Gly Gly Ser Leu Ala
    50                  55                  60

Ala Leu Thr Ala His Gln Ala Cys His Leu Pro Leu Glu Thr Phe Thr
65                  70                  75                  80

Arg His Arg Gln Pro Arg Gly Trp Glu Gln Leu Glu Gln Cys Gly Tyr
                85                  90                  95

Pro Val Gln Arg Leu Val Ala Leu Tyr Leu Ala Ala Arg Leu Ser Trp
            100                 105                 110

Asn Gln Val Asp Gln Val Ile Arg Asn Ala Leu Ala Ser Pro Gly Ser
        115                 120                 125

Gly Gly Asp Leu Gly Glu Ala Ile Arg Glu Gln Pro Glu Gln Ala Arg
    130                 135                 140

Leu Ala Leu Thr Leu Ala Ala Ala Glu Ser Glu Arg Phe Val Arg Gln
145                 150                 155                 160

Gly Thr Gly Asn Asp Glu Ala Gly Ala Ala Asn Ala Asp Val Val Thr
                165                 170                 175

Leu Thr Ala Pro Val Ala Ala Gly Glu Ala Ala Gly Pro Ala Asp Ser
            180                 185                 190

Gly Asp Ala Leu Leu Glu Arg Asn Tyr Pro Thr Gly Ala Glu Phe Leu
        195                 200                 205
```

```
Gly  Asp  Gly  Gly  Asp  Val  Ser  Phe  Ser  Thr  Arg  Gly  Thr  Gln  Asn  Trp
     210                 215                 220

Thr  Val  Glu  Arg  Leu  Leu  Gln  Ala  His  Arg  Gln  Leu  Glu  Glu  Arg  Gly
225                      230                 235                           240

Tyr  Val  Phe  Val  Gly  Tyr  His  Gly  Thr  Phe  Leu  Glu  Ala  Ala  Gln  Ser
               245                      250                           255

Ile  Val  Phe  Gly  Gly  Val  Arg  Ala  Arg  Ser  Gln  Asp  Leu  Asp  Ala  Ile
               260                 265                      270

Trp  Arg  Gly  Phe  Tyr  Ile  Ala  Gly  Asp  Pro  Ala  Leu  Ala  Tyr  Gly  Tyr
          275                      280                      285

Ala  Gln  Asp  Gln  Glu  Pro  Asp  Ala  Arg  Gly  Arg  Ile  Arg  Asn  Gly  Ala
     290                 295                      300

Leu  Leu  Arg  Val  Tyr  Val  Pro  Arg  Ser  Ser  Leu  Pro  Gly  Phe  Tyr  Arg
305                      310                 315                           320

Thr  Ser  Leu  Thr  Leu  Ala  Ala  Pro  Glu  Ala  Ala  Gly  Glu  Val  Glu  Arg
               325                 330                           335

Leu  Ile  Gly  His  Pro  Leu  Pro  Leu  Arg  Leu  Asp  Ala  Ile  Thr  Gly  Pro
          340                      345                      350

Glu  Glu  Glu  Gly  Gly  Arg  Leu  Glu  Thr  Ile  Leu  Gly  Trp  Pro  Leu  Ala
          355                      360                      365

Glu  Arg  Thr  Val  Val  Ile  Pro  Ser  Ala  Ile  Pro  Thr  Asp  Pro  Arg  Asn
     370                      375                 380

Val  Gly  Gly  Asp  Leu  Asp  Pro  Ser  Ser  Ile  Pro  Asp  Lys  Glu  Gln  Ala
385                      390                      395                      400

Ile  Ser  Ala  Leu  Pro  Asp  Tyr  Ala  Ser  Gln  Pro  Gly  Lys  Pro  Pro  Arg
               405                      410                      415

Glu  Asp  Leu  Lys
               420
```

(2) INFORMATION FOR SEQ ID NO:11:

(i) SEQUENCE CHARACTERISTICS:
        (A) LENGTH: 420 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:11:

```
Met  Ala  Ala  Ala  Val  Val  Ser  His  Phe  Asn  Asp  Cys  Pro  Asp  Ser  His
1                   5                   10                      15

Thr  Gln  Phe  Cys  Phe  His  Gly  Thr  Cys  Arg  Phe  Leu  Val  Gln  Glu  Asp
               20                  25                      30

Lys  Pro  Ala  Cys  Val  Cys  His  Ser  Gly  Tyr  Val  Gly  Ala  Arg  Cys  Glu
          35                  40                      45

His  Ala  Asp  Leu  Leu  Ala  Ala  Met  Ala  Glu  Glu  Gly  Gly  Ser  Leu  Ala
     50                  55                      60

Ala  Leu  Thr  Ala  His  Gln  Ala  Ala  His  Leu  Pro  Leu  Glu  Thr  Leu  Thr
65                  70                  75                           80

Arg  His  Arg  Gln  Pro  Arg  Gly  Trp  Glu  Gln  Leu  Glu  Gln  Ala  Gly  Tyr
               85                      90                           95

Pro  Val  Gln  Arg  Leu  Val  Ala  Leu  Tyr  Leu  Ala  Ala  Arg  Leu  Ser  Trp
               100                     105                     110

Asn  Gln  Val  Asp  Gln  Val  Ile  Arg  Asn  Ala  Leu  Ala  Ser  Pro  Gly  Ser
          115                     120                     125

Gly  Gly  Asp  Leu  Gly  Glu  Ala  Ile  Arg  Glu  Gln  Pro  Glu  Gln  Ala  Arg
```

-continued

| | | | | | | | | | | | | | | | |
|---|---|---|---|---|---|---|---|---|---|---|---|---|---|---|---|
| | 130 | | | | | 135 | | | | | 140 | | | | |
| Leu | Ala | Leu | Thr | Leu | Ala | Ala | Ala | Glu | Ser | Glu | Arg | Phe | Val | Arg | Gln |
| 145 | | | | | 150 | | | | | 155 | | | | | 160 |
| Gly | Thr | Gly | Asn | Asp | Glu | Ala | Gly | Ala | Ala | Asn | Ala | Asp | Val | Val | Thr |
| | | | | 165 | | | | | 170 | | | | | 175 | |
| Leu | Thr | Ala | Pro | Val | Ala | Ala | Gly | Glu | Ala | Ala | Gly | Pro | Ala | Asp | Ser |
| | | | 180 | | | | | 185 | | | | | 190 | | |
| Gly | Asp | Ala | Leu | Leu | Glu | Arg | Asn | Tyr | Pro | Thr | Gly | Ala | Glu | Phe | Leu |
| | | 195 | | | | | 200 | | | | | 205 | | | |
| Gly | Asp | Gly | Gly | Asp | Val | Ser | Phe | Ser | Thr | Arg | Gly | Thr | Gln | Asn | Trp |
| | 210 | | | | | 215 | | | | | 220 | | | | |
| Thr | Val | Glu | Arg | Leu | Leu | Gln | Ala | His | Arg | Gln | Leu | Glu | Glu | Arg | Gly |
| 225 | | | | | 230 | | | | | 235 | | | | | 240 |
| Tyr | Val | Phe | Val | Gly | Tyr | His | Gly | Thr | Phe | Leu | Glu | Ala | Ala | Gln | Ser |
| | | | | 245 | | | | | 250 | | | | | 255 | |
| Ile | Val | Phe | Gly | Gly | Val | Arg | Ala | Arg | Ser | Gln | Asp | Leu | Asp | Ala | Ile |
| | | | 260 | | | | | 265 | | | | | 270 | | |
| Trp | Arg | Gly | Phe | Tyr | Ile | Ala | Gly | Asp | Pro | Ala | Leu | Ala | Tyr | Gly | Tyr |
| | | 275 | | | | | 280 | | | | | 285 | | | |
| Ala | Gln | Asp | Gln | Glu | Pro | Asp | Ala | Arg | Gly | Arg | Ile | Arg | Asn | Gly | Ala |
| | 290 | | | | | 295 | | | | | 300 | | | | |
| Leu | Leu | Arg | Val | Tyr | Val | Pro | Arg | Ser | Ser | Leu | Pro | Gly | Phe | Tyr | Arg |
| 305 | | | | | 310 | | | | | 315 | | | | | 320 |
| Thr | Ser | Leu | Thr | Leu | Ala | Ala | Pro | Glu | Ala | Ala | Gly | Glu | Val | Glu | Arg |
| | | | | 325 | | | | | 330 | | | | | 335 | |
| Leu | Ile | Gly | His | Pro | Leu | Pro | Leu | Arg | Leu | Asp | Ala | Ile | Thr | Gly | Pro |
| | | | 340 | | | | | 345 | | | | | 350 | | |
| Glu | Glu | Glu | Gly | Gly | Arg | Leu | Glu | Thr | Ile | Leu | Gly | Trp | Pro | Leu | Ala |
| | | 355 | | | | | 360 | | | | | 365 | | | |
| Glu | Arg | Thr | Val | Val | Ile | Pro | Ser | Ala | Ile | Pro | Thr | Asp | Pro | Arg | Asn |
| | 370 | | | | | 375 | | | | | 380 | | | | |
| Val | Gly | Gly | Asp | Leu | Asp | Pro | Ser | Ser | Ile | Pro | Asp | Lys | Glu | Gln | Ala |
| 385 | | | | | 390 | | | | | 395 | | | | | 400 |
| Ile | Ser | Ala | Leu | Pro | Asp | Tyr | Ala | Ser | Gln | Pro | Gly | Lys | Pro | Pro | Arg |
| | | | | 405 | | | | | 410 | | | | | 415 | |
| Glu | Asp | Leu | Lys | | | | | | | | | | | | |
| | | | 420 | | | | | | | | | | | | |